US00PP16966P3

(12) United States Plant Patent
Ichiba

(10) Patent No.: US PP16,966 P3
(45) Date of Patent: Aug. 8, 2006

(54) ***COSMOS* PLANT NAMED 'STRAWBERRY CHOCO SANSE 41'**

(50) Latin Name: *Cosmos* hybrid
Varietal Denomination: Strawberry Choco Sanse 41

(75) Inventor: Kaori Ichiba, Yamanashi (JP)

(73) Assignee: Miyoshi & Co., Ltd., Tokyo (JP)

( * ) Notice: Subject to any disclaimer, the term of this patent is extended or adjusted under 35 U.S.C. 154(b) by 0 days.

(21) Appl. No.: 11/031,714

(22) Filed: Jan. 6, 2005

(65) Prior Publication Data

US 2005/0160508 P1 Jul. 21, 2005

(30) Foreign Application Priority Data

Jan. 21, 2004 (JP) ..... 16581

(51) Int. Cl.
*A01H 5/00* (2006.01)

(52) U.S. Cl. ..... Plt./226

(58) Field of Classification Search ..... Plt./226
See application file for complete search history.

*Primary Examiner*—Kent Bell
*Assistant Examiner*—Annette H Para
(74) *Attorney, Agent, or Firm*—Christie, Parker & Hale, LLP

(57) ABSTRACT

A new and distinct variety of *Cosmos,* named 'Strawberry Choco Sanse 41', characterized by a very vigorous branching habit, abundance of flowers, high hardiness with high heat resistance, low susceptibility to powdery mildew and mites, large flower size, delayed bloom after pinching and distinctive red color of the flower.

15 Drawing Sheets

Botanical classification: The present invention relates to a new *Cosmos* hybrid.

Cultivar denomination: The new plant has the varietal denomination 'Strawberry Choco Sanse 41'.

BACKGROUND OF THE INVENTION

The new variety of *Cosmos* was created in a controlled breeding program by crossing two parents; in particular, by crossing as seed parent *Cosmos atrosanguineus* and as pollen parent *Cosmos sulphureus*. The breeding program was conducted in Kubuchizawa, Kitakoma-gun, Yamanashi, Japan. The crossing was made in March 2002, and seedlings were transplanted and pinched in early September of the same year. With applied lighting, the first flowers were observed in December 2002 and initial selections were made for new flower color and more vigorous growth. Root cuttings obtained from selected seedlings were planted in September 2003, and final selections for new color and more vigorous growth were made in December 2003.

The resulting seedling of the new variety was grown and asexually propagated by rooted cuttings in Yamanashi, Japan, in March 2004. This propagation and subsequent testing has demonstrated that the combination of traits disclosed herein which characterize the new variety are fixed and retained true to type through successive generations of asexual reproduction.

SUMMARY OF THE INVENTION

The present invention relates to a new and distinct *Cosmos* variety. The varietal denomination of the new variety is 'Strawberry Choco Sanse 41'. Among the characteristics which appear to distinguish the new variety from other varieties are a very vigorous branching habit, abundance of flowers, high hardiness with high heat resistance, low susceptibility to powdery mildew and mites, large flower size, delayed bloom after pinching and distinctive red color of the flower.

COMPARISON TO CLOSEST VARIETY

The new variety is closest to *Cosmos atrosanguineus,* but is distinguished therefrom by the following characteristics possessed by 'Strawberry Choco Sanse 41' which are different than, or not possessed by, *C. atrosanguineus:*

- Very vigorous branching habit (8 to 10 branches per plant compared to 4 to 5 branches for *C. atrosanguineus*)
- Abundance of flowers (8 to 10 flowers per plant compared to 4 to 5 flowers for *C. atrosanguineus*)
- Rapid growth and establishment (Diameter 10 to 15 cm, thirty days after planting, compared to 8 to 10 cm, thirty days after planting, for *C. atrosanguineus*)
- Distinctive red color of the flower (Grayed purple color near RHS 187B, compared to Grayed purple color near RHS 187A for *C. atrosanguineus*)
- Different flowering time (80 to 90 days after pinching, compared to 60 to 70 days after pinching for *C. atrosanguineus*).

PARENT VARIETY COMPARISON

Female parent: *C. atrosanguineus.*

The new variety differs from the female parent in the following characteristics:

1. Much more vigorous branching habit
2. Greater number of flowers per plant
3. Different leaf shape
4. Greater heat tolerance; plants grow over summer without dying. Also, more tolerant to powdery mildew and mites.

5. Flower color is lighter than that of the female parent. Male parent: *C. sulphureus*.

The new variety differs from the male parent in the following characteristics:

1. The male parent is annual while 'Strawberry Choco Sanse 41' is perennial.
2. Male parent flower color is orange while 'Strawberry Choco Sanse 41' has dark red flowers.
3. 'Strawberry Choco Sanse 41' has more branches (8–10 branches per plant) than the male parent (3–5 branches per plant).
4. Flower shape is different.
5. Leaf shape is different.

COMPARISON TO 'CACAO CHOCO SANSE 35'

1. 'Strawberry Choco Sanse 41' has a more reddish brown petal color (near RHS 187B when fully opened) while 'Cacao Choco Sanse 35' has a darker brown petal color (near RHS 187A when fully opened).
2. The flowers of 'Strawberry Choco Sanse 41' are slightly smaller (about 5 mm less in diameter) than those of 'Cacao Choco Sanse 35'.
3. The number of petals in 'Strawberry Choco Sanse 41' is typically around 8 while 'Cacao Choco Sanse 35' typically has 0 to 10 petals.
4. 'Strawberry Choco Sanse 41' flowers about 10 days earlier than 'Cacao Choco Sanse 35'.

BRIEF DESCRIPTION OF ILLUSTRATIONS

DESCRIPTION OF THE NEW VARIETY

The following detailed description of the new variety is based upon observations taken of plants grown outdoors in 30-cm pots in Kubuchizawa, Kitakoma-gun, Yamanashi, Japan, with a range of day temperatures from 18° to 28° Celsius, and a range of night temperatures from 10° to 18° Celsius.

The following description is in accordance with UPOV terminology and the color terminology herein is in accordance with The Royal Horticultural Society Colour Chart (R.H.S.). The color descriptions and other phenotypical descriptions may deviate from the stated values and descriptions depending upon variation in environmental, seasonal, climatic and cultural conditions.

Figure 1:
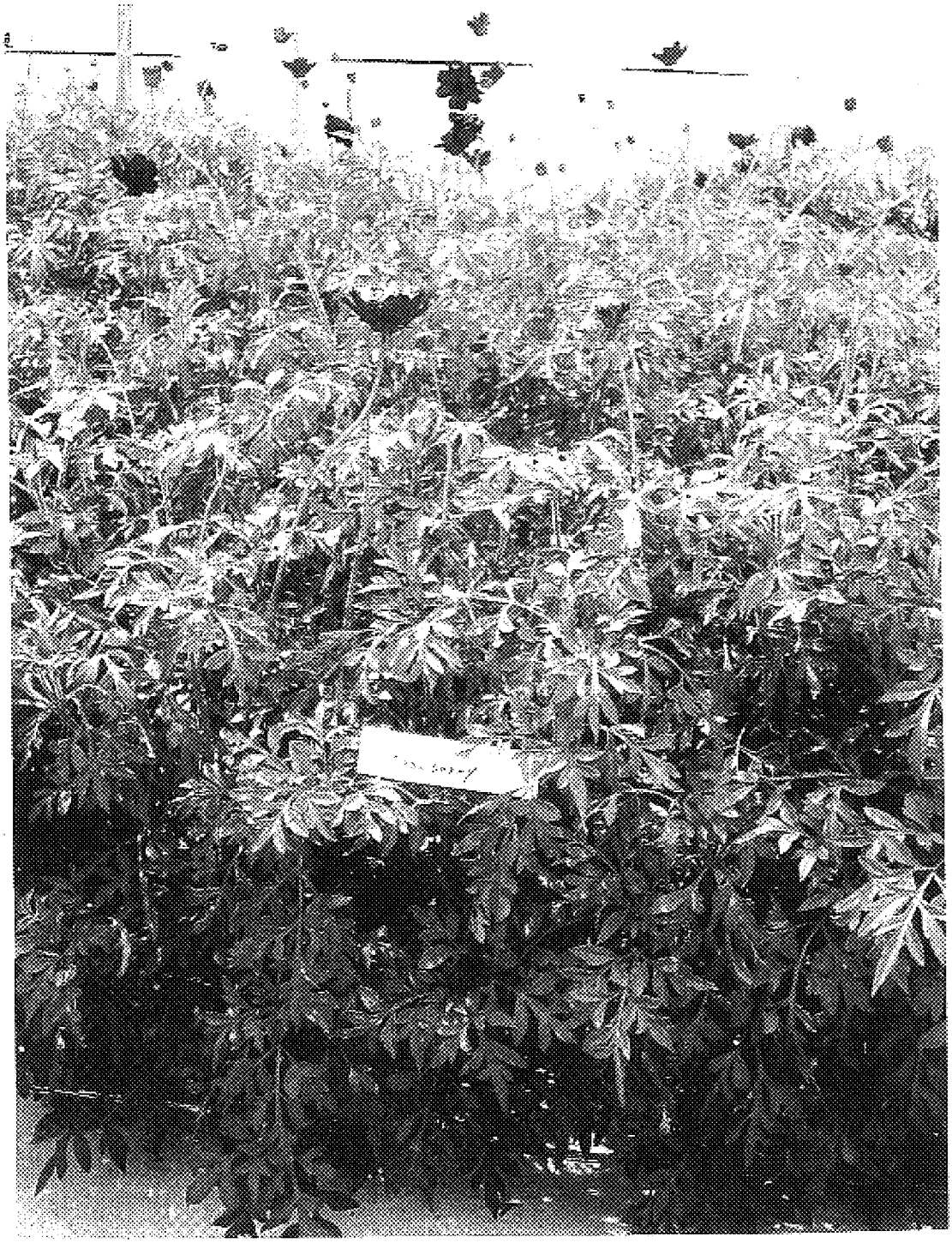
FIG. 1 shows a plant of the new variety.
Figure 2:
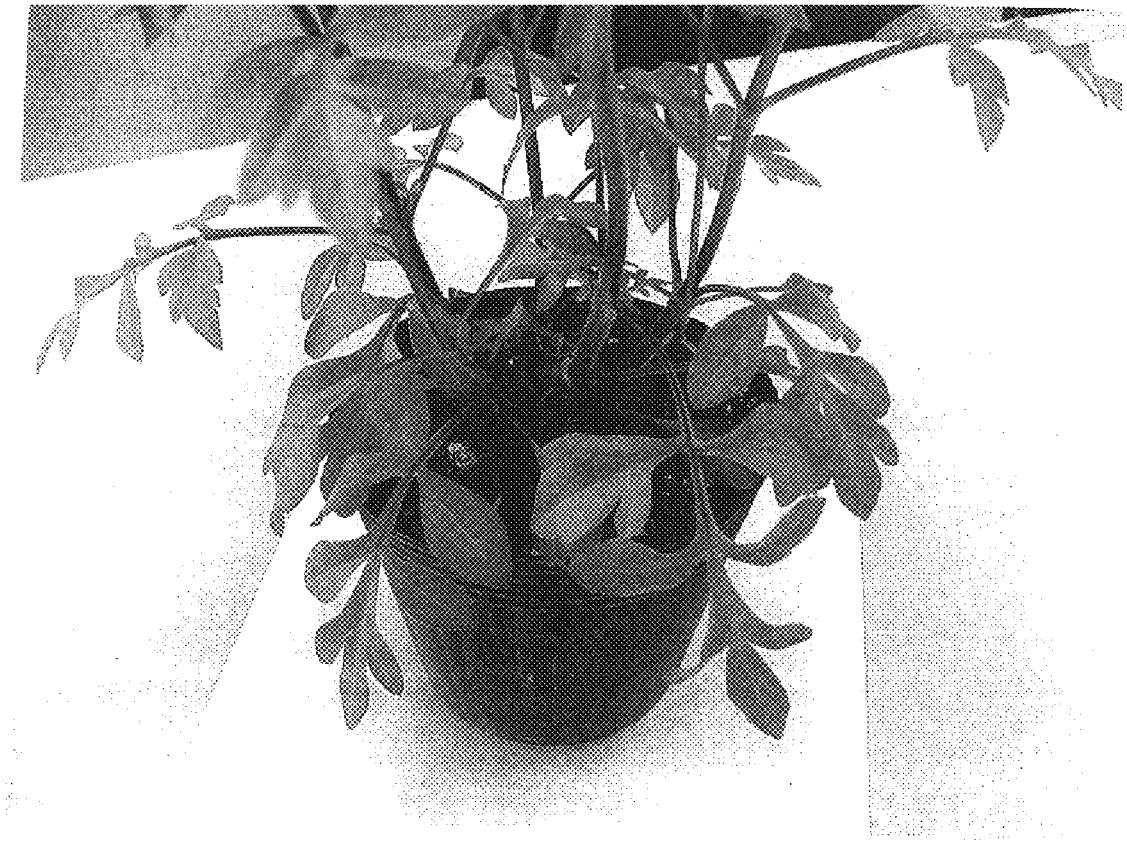
FIG. 2 shows the stems and leaves of the new variety.

Plant: When grown at a temperature between −3° and 30° Celsius, the new variety can be grown as perennial.
- *Shape.*—Spreading or clump forming, as shown in FIG. 1.
- *Height.*—About 30 to 40 cm.
- *Diameter.*—About 20 to 25 cm.
- *Growth rate.*—Grows to about 25 to 30 cm in two months after planting in soil.

Roots:
- *Time to initiate.*—About 30 days.
- *Form.*—Tuberculate.

Branches:
- *Habit.*—Many branches, with about 8 to 10 lateral branches per plant; stems are hard.
- *Length.*—About 30 to 40 cm.
- *Diameter.*—About 5 to 8 mm.
- *Internode length.*—About 3 to 5 cm.
- *Color.*—Grayed purple group, near R.H.S. 187B.
- *Pubescence.*—Present.

Figure 3:
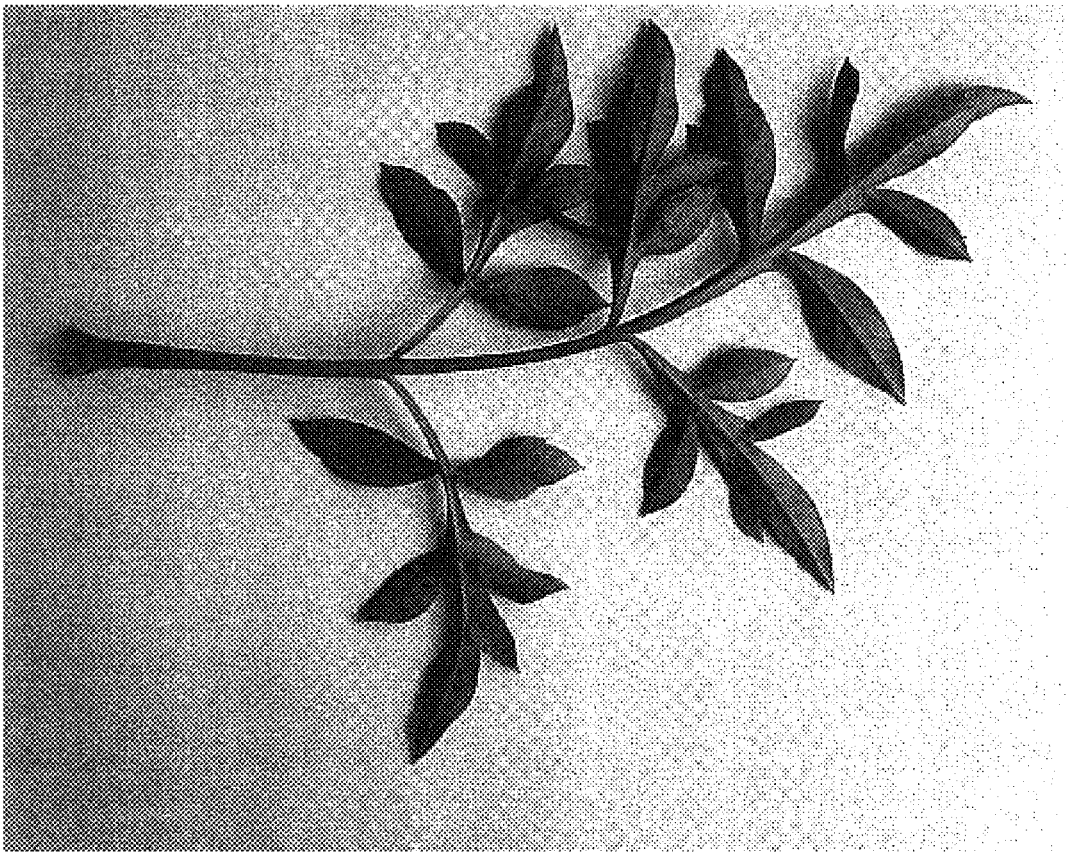
FIG. 3 shows the underside of a leaf of the new variety.
Figure 4:
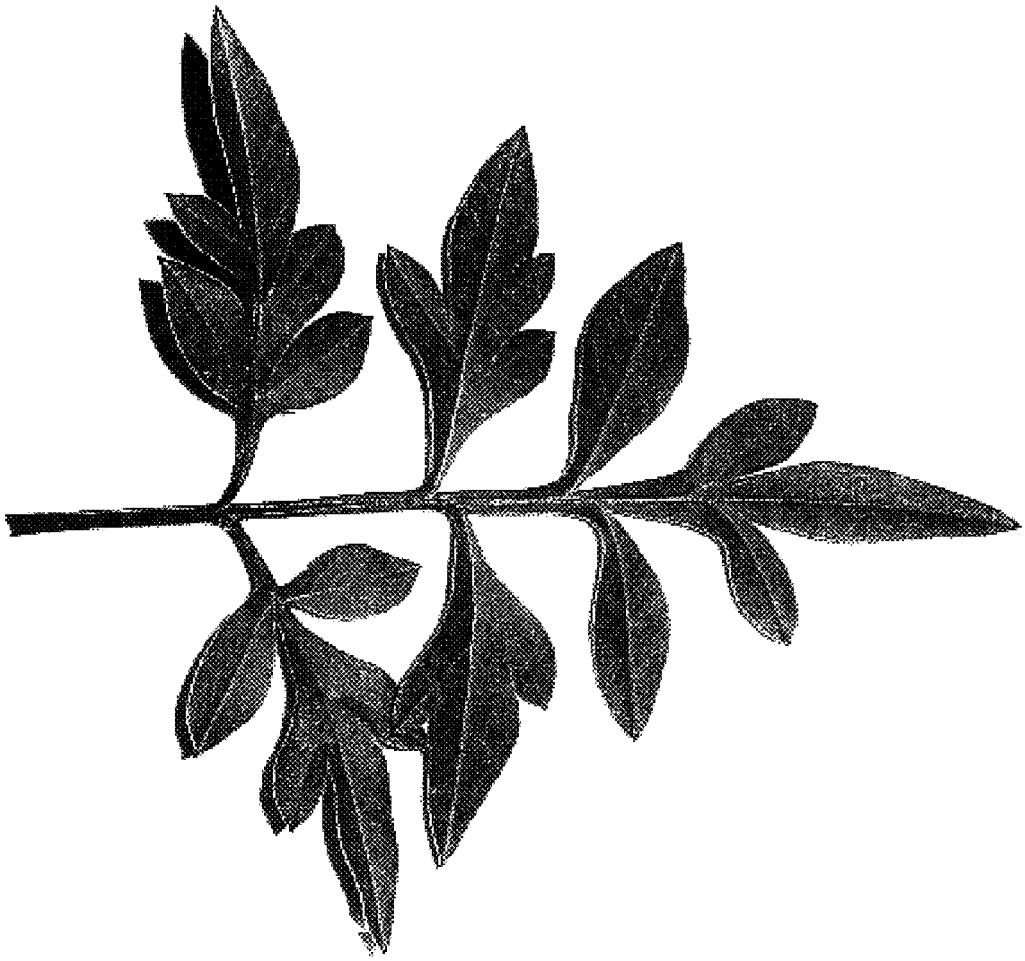
FIG. 4 shows the upperside of a leaf of the new variety.
Figure 5:
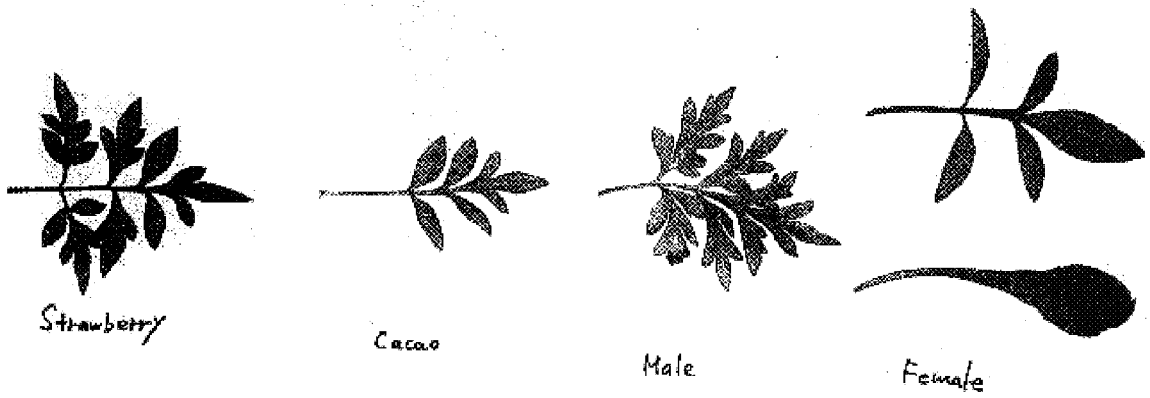
FIG. 5 shows the leaf of the new variety compared to leaves of the male and female parent and the variety 'Cacao Choco Sanse 35'.
Figure 6:
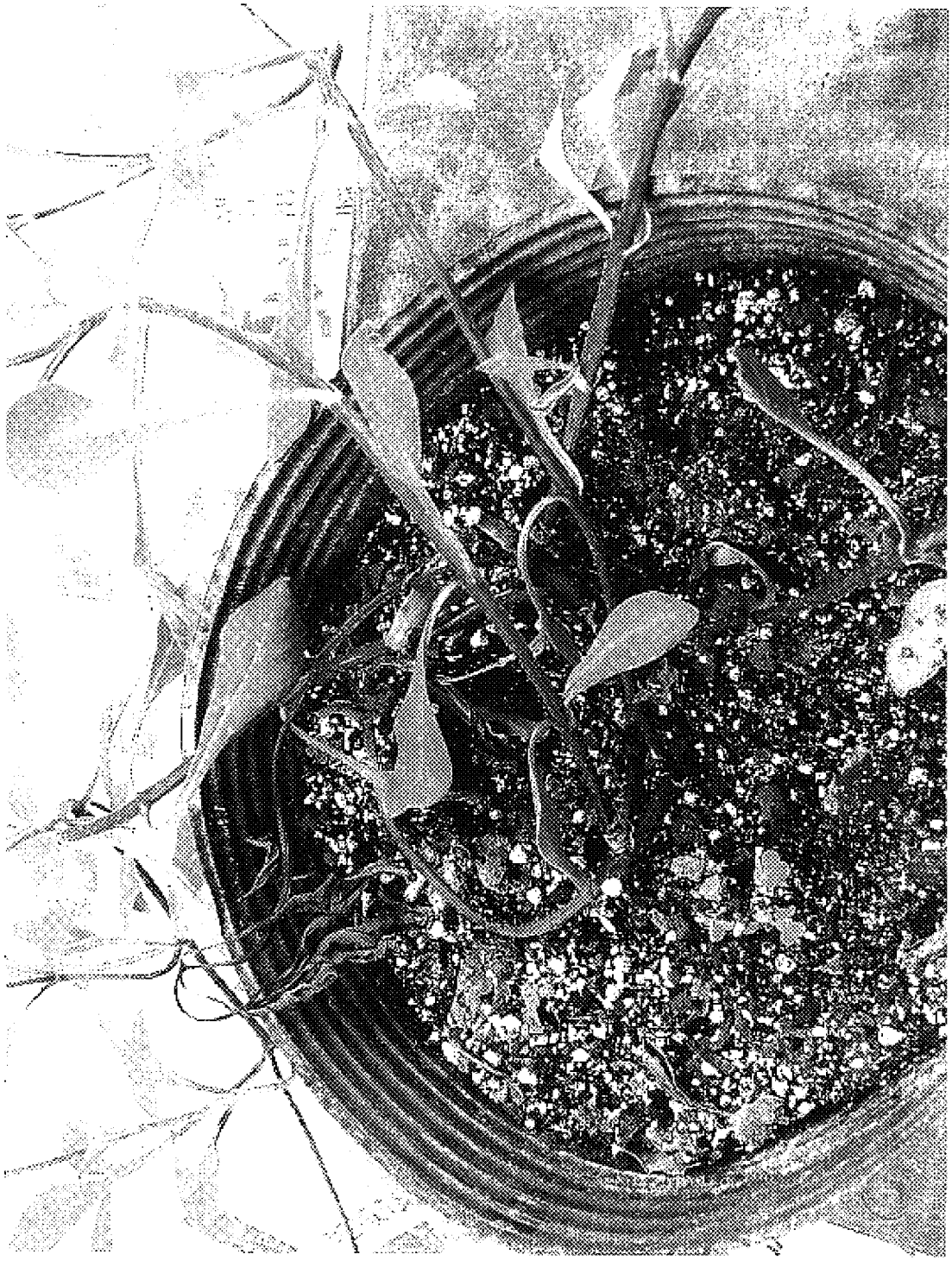
FIG. 6 shows a plant of the female parent *C. atrosanguineus*.
Figure 7:
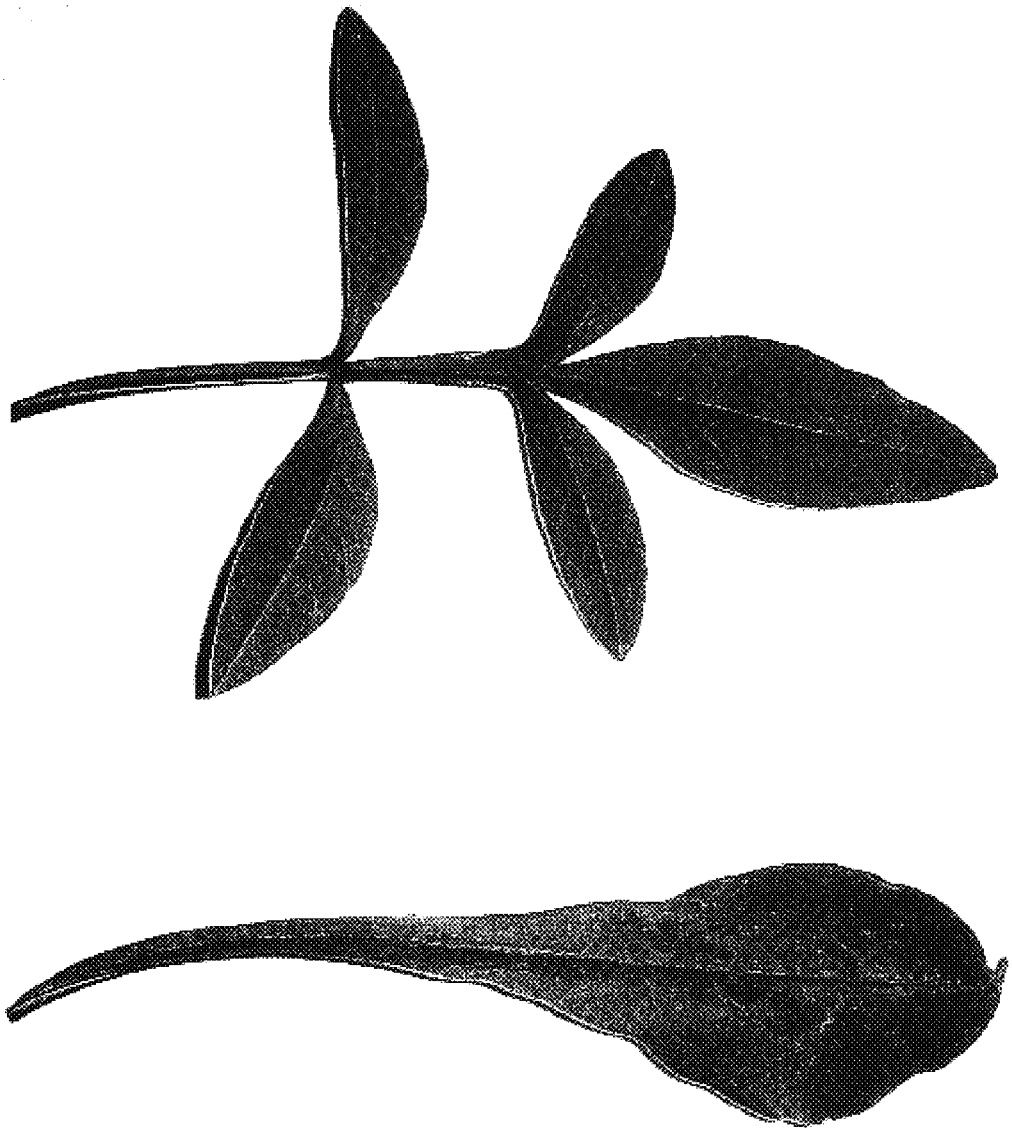
FIG. 7 shows the upperside of a leaf of the female parent *C. atrosanguineus*.
Figure 8:
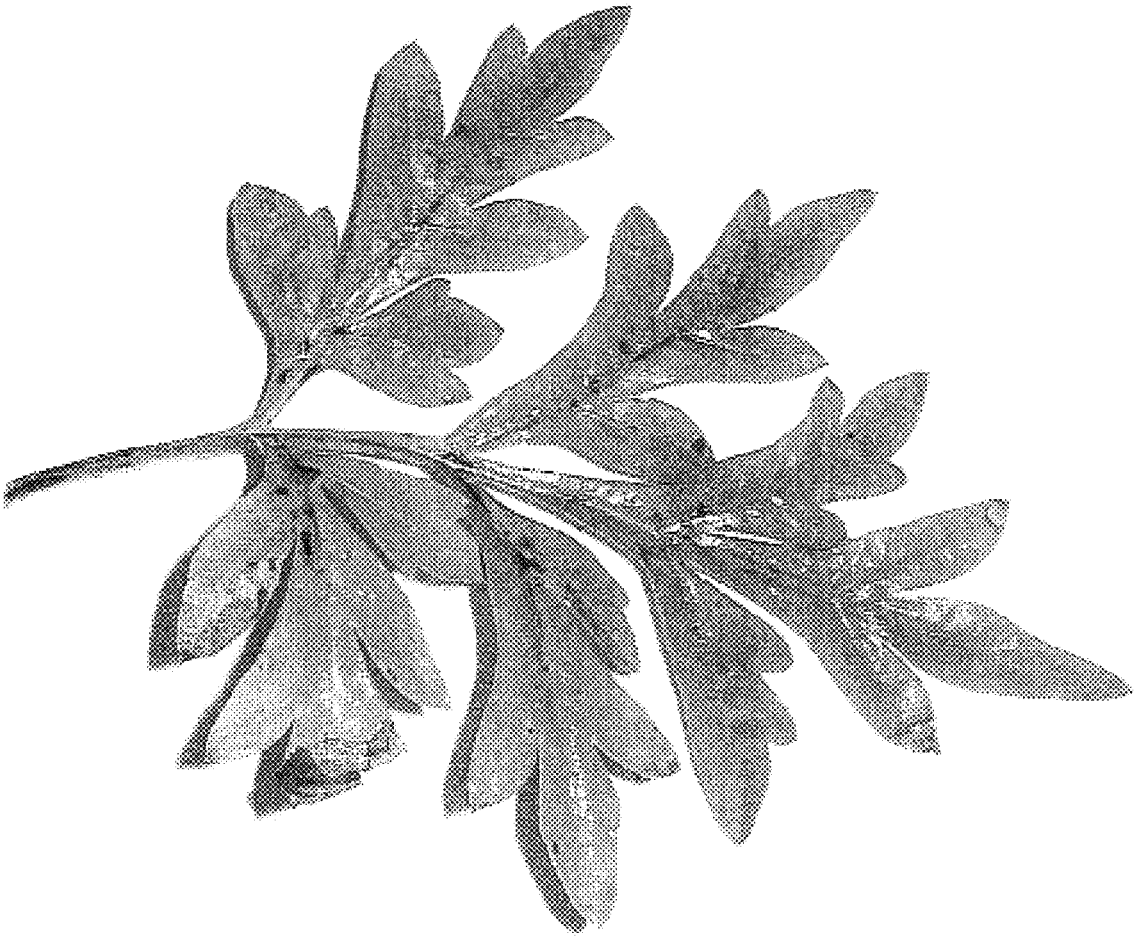
FIG. 8 shows the upperside of a leaf of the male parent *C. sulphureus*.
Figure 9:
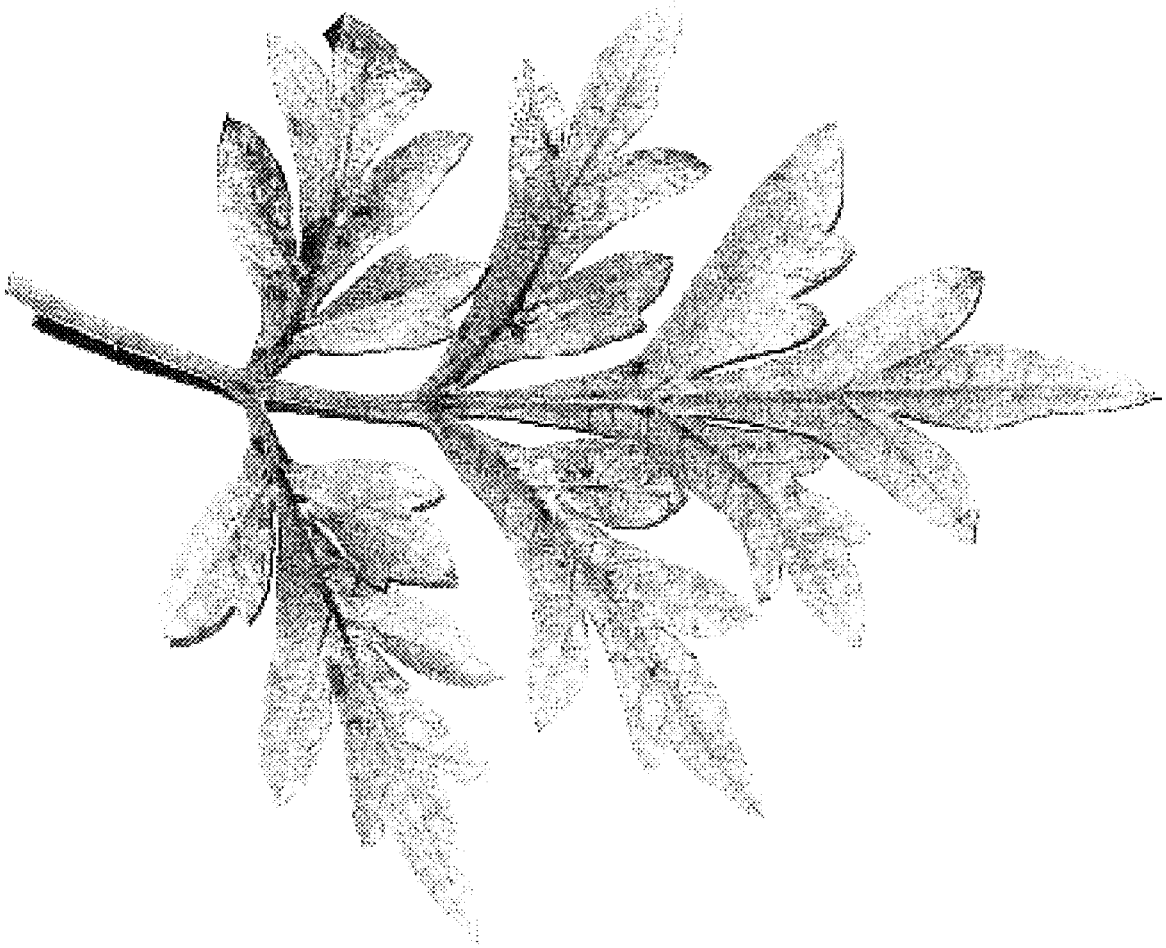
FIG. 9 shows the underside of a leaf of the male parent *C. sulphureus*.
Figure 10:
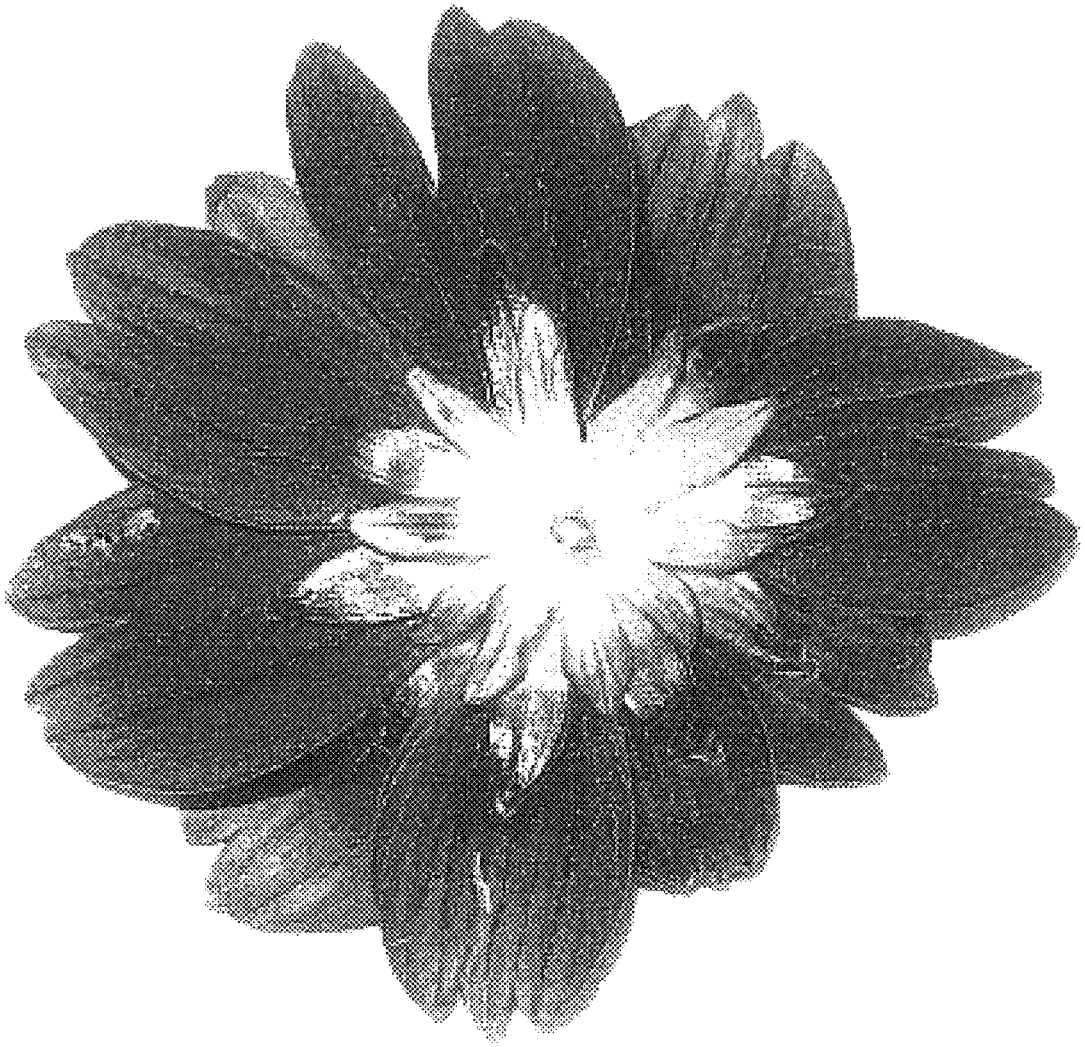
FIG. 10 shows the calyx of the new variety.
Figure 11:
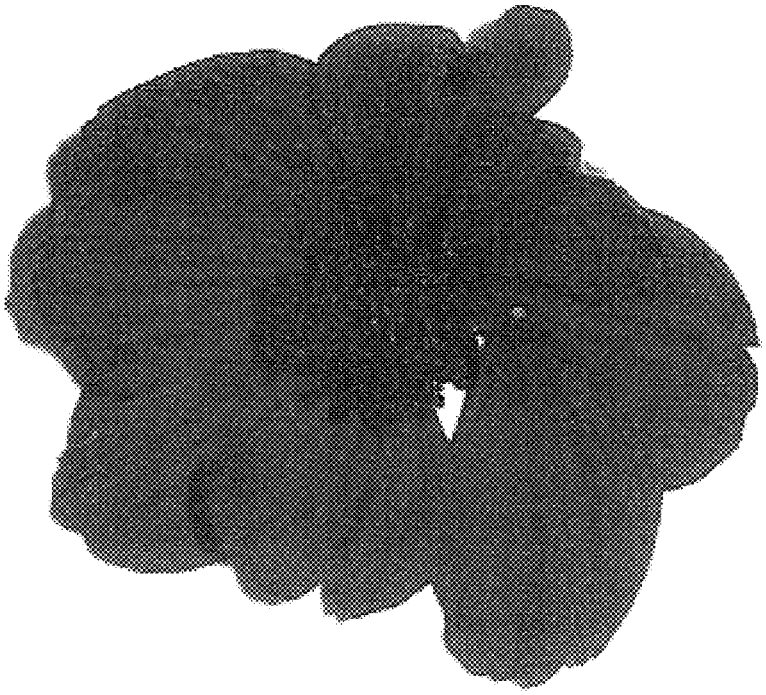
FIG. 11 shows the corolla of the new variety.
Figure 12:
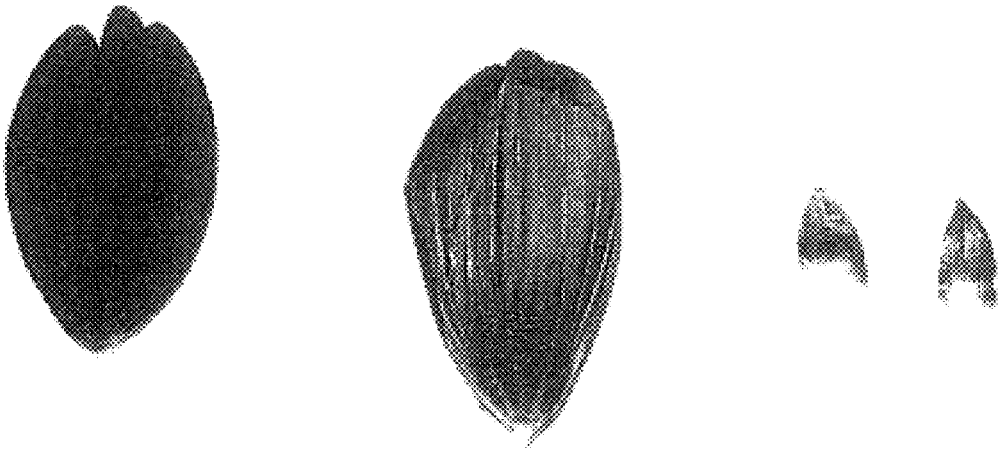
FIG. 12 shows petals of the new variety.
Figure 13:
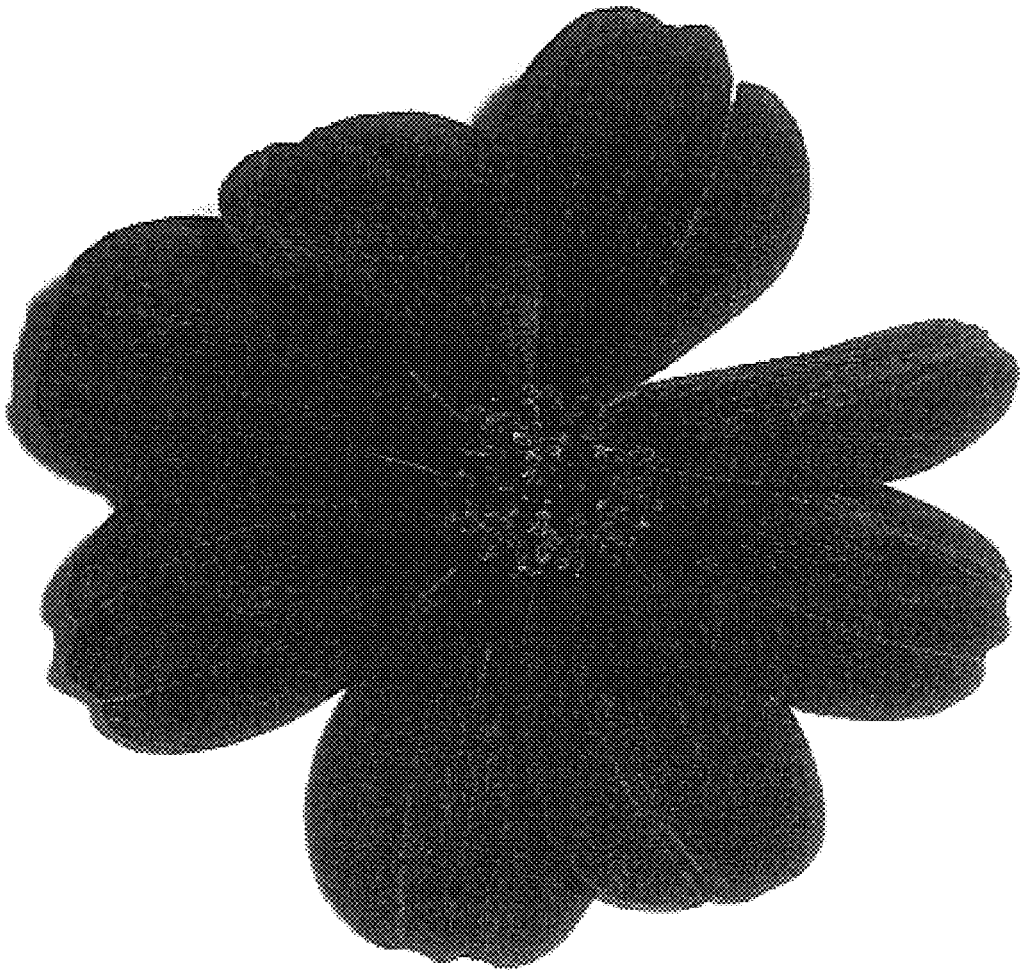
FIG. 13 shows the corolla of the female parent, *C. atrosanguineus,* of the new variety.
Figure 14:
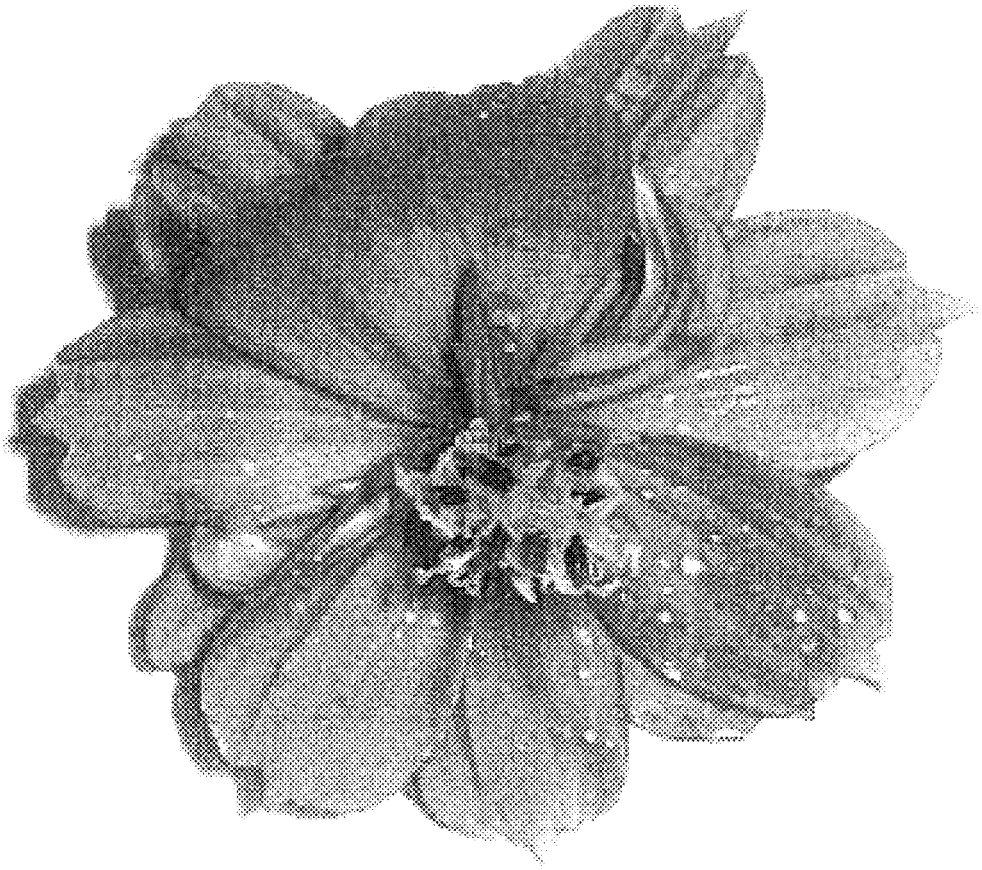
FIG. 14 shows the corolla of the male parent, *C. sulphureus,* of the new variety.
Figure 15:
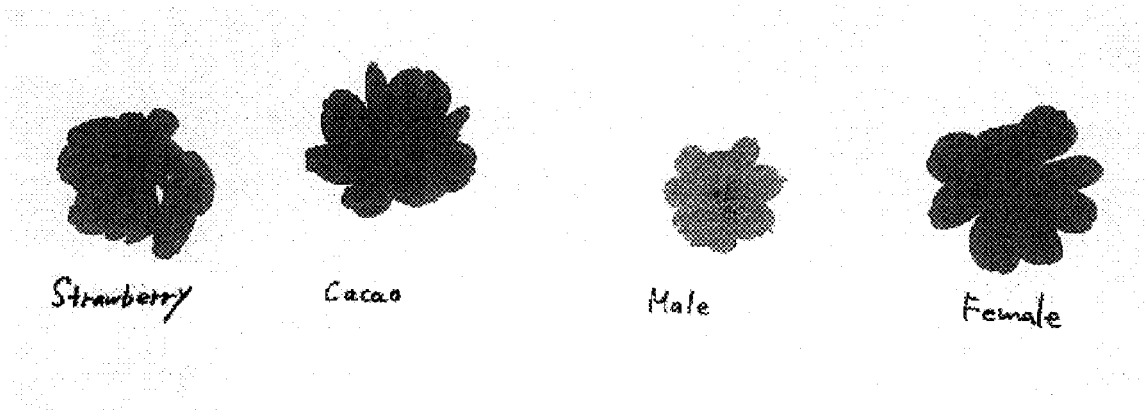
FIG. 15 shows the corolla of the new variety compared to corolla of the male and female parent and the variety 'Cacao Choco Sanse 35'.
Figure 16:
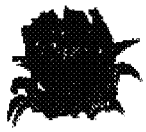
FIG. 16 shows a bud of the new variety compared to a bud of the variety 'Cacao Choco Sanse 35'.
Figure 16:
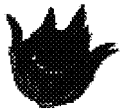

Foliage:
- *Leaf arrangement.*—Decussate opposite, as shown in FIG. 3.
- *Number.*—About 8 to 12 leaves per lateral branch.
- *Form.*—Compound, with 5 leaflets per leaf.
- *Leaflet shape.*—Dissected, with acute tip and attenuate base.
- *Size.*—About 8 to 10 cm in length, about 4–6 cm in width.
- *Texture.*—Opaque, not glossy, with some pubescence on the underside.
- *Margin.*—Entire.
- *Venation.*—Palmate.
- *Color, young.*—Upperside, Yellow green group, near R.H.S. 144B; underside, Yellow green group, near R.H.S. 144C.
- *Color, mature.*—Upperside, Yellow green group, near R.H.S. 144A; underside, Yellow green group, near R.H.S. 144B.
- *Vein color.*—Upperside, Grayed purple group, near R.H.S. 187B; underside, Grayed purple group, near R.H.S. 187B; but slightly lighter than upperside.
- *Petiole size.*—Length, about 1.5 to 3.0 cm; diameter, about 3 to 5 mm.
- *Petiole color.*—Light reddish brown, near Grayed purple group R.H.S. 187C.

Flower:
- *Arrangement.*—Solitary.
- *Form.*—Cup shaped.
- *Flowering habit.*—Long day plant, normally flowering in June and July.
- *Time to flower.*—About 80 to 90 days after pinching.
- *Number.*—One flower per lateral stem; 2 to 4 buds per lateral stem; about 13 to 20 flowers and buds per plant.

*Size.*—Diameter, about 5 to 6 cm; depth, about 1.5 to 2.0 cm.

*Fragrance.*—Soft fragrance.

*Lastingness of bloom.*—On plant, Spring planting, about 120 to 150 days, Autumn planting, about 50 to 90 days; cut flower, about 7 to 10 days.

*Number of petals.*—About 8 per flower.

*Petal texture.*—Velvety.

*Petal size.*—Length, about 2.5 cm; width, about 2.0 cm.

*Petal color.*—When opening Upperside, Grayed purple group, near R.H.S. 187A, underside, Grayed purple group, near R.H.S. 187B; Fully opened Upperside, Grayed purple group, near R.H.S. 187B, underside, Grayed purple group, near R.H.S. 187C.

*Number of sepals.*—About 10 per flower.

*Sepal color.*—Upperside, Green group, near R.H.S. 137C, underside, Green group, near R.H.S. 137C.

*Calyx size.*—Length, about 1.0 to 1.2 cm, diameter, about 2.0 to 2.3 cm.

*Peduncle length.*—About 15 to 20 cm.

*Peduncle color.*—Yellow green group, near R.H.S. 146D.

*Flower bud size.*—Length, about 0.8 to 1.2 cm; diameter, about 0.8 to 1.2 cm.

*Bud opening rate.*—About 70% to 80%.

*Flower bud color.*—Grayed purple group near R.H.S. 187 A.

*Stamen.*—Degenerated.

*Anther.*—Degenerated.

*Pistil.*—Number, about 30 to 50 per flower; length, about 5 to 8 mm.

*Stigma.*—Color, Yellow group, near R.H.S. 13A.

*Style.*—Length, about 0.8 to 1.0 mm; color, Yellow group, near R.H.S. 13A.

*Ovary.*—Color, light yellow, near R.H.S. 154D; no seed development.

Disease resistance: Increased tolerance to powdery mildew and mites.

Heat tolerance: Increased heat tolerance; plants grow over summer without dying.

I claim:

1. A new and distinct variety of *Cosmos* plant, identified as 'Strawberry Choco Sanse 41', substantially as shown and described.

* * * * *

Strawberry

CaCao